(12) United States Patent
Sedky et al.

(10) Patent No.: US 12,310,894 B2
(45) Date of Patent: May 27, 2025

(54) POST-TREATMENT IN REFRACTION CORRECTION DURING EYE SURGERY

(71) Applicant: Carl Zeiss Meditec AG, Jena (DE)

(72) Inventors: Ahmed Sedky, Heliopolis Cairo (EG); Mark Bischoff, Jena (DE); Matthias Wottke, Postbauer-Heng (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/523,294

(22) Filed: Nov. 29, 2023

(65) Prior Publication Data

US 2024/0091064 A1 Mar. 21, 2024

Related U.S. Application Data

(63) Continuation of application No. 16/610,226, filed as application No. PCT/EP2018/061337 on May 3, 2018, now Pat. No. 11,864,979.

(30) Foreign Application Priority Data

May 4, 2017 (DE) ..................... 10 2017 207 529.5

(51) Int. Cl.
*A61F 9/008* (2006.01)
(52) U.S. Cl.
CPC ............. *A61F 9/00827* (2013.01); *A61F 2009/00861* (2013.01); *A61F 2009/00872* (2013.01); *A61F 2009/0088* (2013.01); *A61F 2009/00882* (2013.01); *A61F 2009/00897* (2013.01)

(58) Field of Classification Search
CPC ........ A61F 9/00827; A61F 2009/00861; A61F 2009/00872; A61F 2009/0088; A61F 2009/00882; A61F 2009/00897
See application file for complete search history.

(56) References Cited

U.S. PATENT DOCUMENTS

| | | | |
|---|---|---|---|
| 9,655,512 B2 | 5/2017 | Huang | |
| 2004/0116910 A1 | 6/2004 | Markman | |
| 2007/0282313 A1 | 12/2007 | Huang | |
| 2008/0287929 A1 | 11/2008 | Holliday | |
| 2011/0224658 A1 | 9/2011 | Bischoff et al. | |
| 2014/0155875 A1 | 6/2014 | Bergt | |
| 2017/0143544 A1 | 5/2017 | Holliday | |

FOREIGN PATENT DOCUMENTS

| | | |
|---|---|---|
| DE | 69500997 T2 | 4/1988 |
| DE | 103 23 422 A1 | 4/2004 |

(Continued)

OTHER PUBLICATIONS

International Search Report and Written Opinion for International Application No. PCT/EP2018/061337, mailed Aug. 24, 2018, 14 pages.

(Continued)

*Primary Examiner* — Lynsey C Eiseman
*Assistant Examiner* — Skylar Lindsey Christianson
(74) *Attorney, Agent, or Firm* — DeWitt LLP

(57) ABSTRACT

A planning device for generating control data, a treatment apparatus for refraction correction eye surgery and a method for generating control data for such a treatment apparatus which allows an improved subsequent refraction correction. The planning device includes a calculation processor for defining a cut surface of the cornea for post-treatment, wherein the calculation device is designed such that a change of thickness of the epithelium is taken into account in the calculation, which was caused essentially by a pre-treatment.

18 Claims, 5 Drawing Sheets

(56) References Cited

FOREIGN PATENT DOCUMENTS

| | | |
|---|---|---|
| DE | 10 2005 040338 A1 | 3/2007 |
| DE | 10 2007 019813 A1 | 3/2007 |
| DE | 10 2007 019 814 A1 | 10/2008 |
| DE | 10 2011 083 928 A1 | 4/2013 |
| DE | 10 2012 022081 A1 | 5/2014 |
| DE | 10 2015 218 909 A1 | 3/2017 |
| EP | 343 432 A2 | 11/1989 |
| WO | WO 2016/144404 A1 | 9/2016 |

OTHER PUBLICATIONS

English translation of International Search Report for International Application No. PCT/EP2018/061337, mailed Aug. 24, 2018, 3 pages.
German Search Report for Application No. 10 2017 207 529.5 dated Aug. 1, 2018, 16 pages.
"Refractive Surface Alation: PRK, LASEK, Epi-lasik, Custom, PTK, and Retreatment" by Paolo Vinciquerra, Fabrizio Camesasca—Chapter 36 Dan Z. Reinstein, Ronald H. Silverman, Timothy J. Archer—"Very high frequency digital ultrasound: artemis 2 scanning in corneal refractive surgery," SLACK Inc. Thorofare, NJ, USA, 2007.
Luft et al., "Corneal epithelial remodeling induced by Small Incision Lenticular Extraction (SMILE)," Invest Ophthalmol Vis Sci., Issue 47, No. 9, pp. 176-183, 2016.
Ganesh, "Epithelial thickness Profile Change Following Small Incision Refractive Lenticule Extraction (SMILE) for Myopia and Myopic Astimatism," JRS, Issue 32, No. 7, pp. 473-478, 2016.
International Preliminary Report on Patentability for International Application No. PCT/EP2018/061337, mailed Mar. 5, 2018, 7 pages.

POST-TREATMENT IN REFRACTION CORRECTION DURING EYE SURGERY

RELATED APPLICATIONS

This application is a continuation of U.S. patent application Ser. No. 16/610,226, filed Nov. 1, 2019, which in turn is a National Phase entry of PCT Application No. PCT/EP2018/061337 filed May 3, 2018, which application claims the benefit of priority to DE Application No. 10 2017 207 529.5, filed May 4, 2017, the entire disclosures of which are incorporated herein by reference.

TECHNICAL FIELD

The invention relates to a planning device for generating control data for a treatment device, which generates at least one incision in the cornea by application of a laser device. The invention also relates to a treatment device that has a planning device of the type specified. The invention also relates to a method for generating control data for a treatment device, which generates at least one incision in the cornea by application of a laser device. Lastly, the invention also relates to a method for eye surgery, wherein at least one incision is generated in the cornea by application and will of a treatment device that has a laser device.

BACKGROUND

A variety of treatment methods for refraction correction in the human eye are known from the prior art. The aim of the surgical method is to modify the cornea in a targeted manner, in order to thus have an effect on the refraction in the eye. Numerous surgical methods are used for this. The most common method currently is so-called laser-assisted in situ keratomileusis, also known as LASIK. For this, a flap of cornea is first separated from the cornea surface at one side, and folded back. The separation of this flap can be achieved by application of a mechanical microkeratome, or by application of a so-called laser keratome, e.g., from Intralase Corp. in Irvine California, USA. After the flap has been separated and folded to the side, the cornea tissue under the flap that has been exposed is removed by ablation. After the volume lying beneath the surface of the cornea has been vaporized in this manner, the cornea flap is folded back over the original area.

The use of a laser keratome for separating the flap is advantageous in comparison with a mechanical blade because the geometric precision is improved, and the frequency of clinically relevant complications is reduced. In particular, the flap can be obtained with a much more uniform thickness when a laser beam is used. The edge of the cut is also precise, reducing the risk of healing disruptions caused by this border surface, which remains after the operation. The disadvantage with this method is that two different treatment devices have to be used, specifically the laser keratome for separating the flap, and the laser for vaporizing the cornea tissue.

These disadvantages are eliminated with a method recently implemented by the Carl Zeiss Meditec AG, referred to with the abbreviated term FLEX. A cutting geometry is formed with this method for lenticule extraction in the cornea by application of a short pulse laser, for example a femtosecond laser, which separates a cornea volume (so-called lenticule) in the cornea. This is then manually removed by the surgeon after the flap covering the lenticule as been folded to the side. The advantage with this method is that the precision of the operation is further improved through the use of the femtosecond laser. Moreover, only one treatment device is necessary, because the excimer laser is no longer used.

A further development of the FLEX method is called the SMILE method, in which a flap is not generated, and instead, just a small hole is cut in order access the lenticule beneath the so-called cap. The separated lenticule is removed through this small hole, such that the biomechanical integrity of the frontal cornea is impaired less than with LASIK, FLEX or PRK (photorefractive keratectomy). Furthermore, fewer surface nerve fibers are cut as a result, which has proven to be beneficial in restoring the original sensitivity in the cornea surface. The dry eye symptoms that frequently require treatment after LASIK surgery are reduced as a result, both in terms of their severity and their duration. Other complications following LASIK surgery, usually in conjunction with the flap (e.g., creases, epithelial ingrowths in the flap bed) are less frequent without a flap.

When generating incisions in the cornea by application of a laser beam, the optical beam effect is normally exploited such that an optical breach is generated by a single optical pulse, the length of which can be between approx. 100 fs and 100 ns. It is also known to introduce single concealed pulses into the tissue or material, the energy of which is lower than a threshold value for an optical breach, such that this also results in a material or tissue separation. The concept of generating the incision in the cornea tissue by application of a planar serial focus (focus points) of ultrashort laser pulses allows for numerous types of incisions.

Post-treatment or renewed treatment may be necessary. The reasons for this can be, e.g., that the original treatment had to be aborted, or that the refraction of the eye has changed so much that a new refraction correction becomes necessary. A solution for this is known for the FLEX method in the prior art (DE 10 2007 019814 A1, the entirety of which is referenced hereby). This is based on placing the new incisions such that they do not intersect with the prior operative incisions. This solution can also be used for the SMILE method. It was proposed, however, in DE 2012 022 081 A1, the entirety of which is incorporated by referenced hereby, to determine the position of the prior operative incision through measurements, and to take these into account in making improvements. It has proven, however, to be the case that the measurement of the prior operative incision is associated with a number of practical difficulties. There is therefore reason to conclude that the correction process according to the prior art has not always produced optimal results and is also complicated.

SUMMARY OF THE INVENTION

Example embodiments of the invention of the invention include a planning device for generating control data, a treatment device for refraction correction eye surgery, and a method for generating control data for such a treatment device, which enables an improved subsequent refraction correction, which is also feasible for users of the SMILE method with currently available diagnosis devices.

The inventors have realized that by removing a lenticule from the cornea with a SMILE method, there can be a change in the thickness of the cornea, in particular a thickening of the epithelium of the cornea, which must be taken into account in planning the post-treatment. As a result, the complicated and often less accurate direct determination of the position of the prior operative incision is no longer entirely necessary, in contrast to the earlier methods.

As a result, according to an example embodiment of the invention with a planning device of the type specified in the introduction, contains calculating software or hardware for determining the position of a corneal incision for post-treatment, wherein the calculating software or hardware is configured to take a change in thickness into account in the calculation, in particular an increase in the thickness of the epithelium, substantially caused by a previous treatment (primary treatment).

A problem addressed by the invention is also solved with a treatment device that has a laser device, by application of which laser beams separate at least one incision in the cornea according to control data, and a planning device according to the type specified above, for generating control data, wherein the planning device is configured such that a change in thickness, in particular a thickening of the epithelium, is taken into account in the planning.

A problem addressed by the invention is also solved with a method for generating control data according to the type specified in the introduction, that comprises: determining the change in thickness in the epithelium, and generating a control data set for the cornea incision for actuating the laser device, wherein the change in thickness in the epithelium is taken into account.

A problem addressed by the invention is also solved with a method that comprises: determining the change in thickness in the epithelium, generating a control data set for the cornea incision, transmitting the control data to a treatment device, and generating the incisions by actuating the laser device with the control data set, wherein the change in thickness in the epithelium is taken into account when generating the control data set.

A number of measurement devices or measurement apparatuses can be used for measuring the change in thickness in the epithelium, e.g., OCT (Optical Coherence Tomography), ultrasound, a confocal laser scanning system, a Scheimpflug camera, etc. The important thing is that the measurement precision is greater than or equal to 2 µm. The measurement can take place independently of the post-treatment, thus as the basis for an upcoming planning. Alternatively, the measurement can take place in the therapy device, by application of a measurement device integrated in the therapy device. The measurement device for example enables the measurement of the epithelium thickness to take place during the post-treatment, basically in real time. As a result, the measurement device and the treatment laser can be geometrically aligned, thus resulting in a fixed coordinate relationship between the diagnosis device and the therapy device.

A variation on the determination of the change in thickness comprises a comparative measurement of the epithelium thickness prior to the primary treatment and the secondary treatment.

If the measurement is to take place in advance, the measurement value must be assigned to a coordinate system for the target coordinates of the treatment laser, for which electronic data transmission and registry solutions can be advantageously used.

As an alternative to a measurement, the epithelium growth or epithelium thickness can also be determined through a priori knowledge, estimation, a nomogram, etc. This knowledge should be present in the planning device, for example, in the form of programming code. In particular, typical changes in thickness after a primary treatment should then be derived automatically from information regarding the primary treatment. This is advantageous in that the relationship between different features of the eye that is being treated (e.g. age, size, refraction) and the primary treatment (change in refraction, size of the optical zone, position of the access incision) represents a significant effort for the user in predicting a typical change in thickness after a primary treatment. Even more important, however, is to minimize the risk of a planning error in such a medical treatment, such as may occur when confusing variables or if there is a calculating error.

The change in thickness ΔThickness is also generally a function of the location on the surface of the eye that is to be treated, thus ΔThickness (x, y) or ΔThickness (r, ϕ)). Dealing with such a two dimensional profile and the correct location reference is a challenge for the user, which can be substantially reduced through a corresponding knowledge of the planning device in the form of programming code.

It is to be understood that the features specified above and still to be explained below can be used not only in the specified combinations, but also in other combinations, or in and of themselves, without abandoning the framework of the present invention.

BRIEF DESCRIPTION OF THE DRAWINGS

The invention shall be explained in greater detail below based on the attached drawings, which disclose features substantial to the invention. Therein.

DETAILED DESCRIPTION

Figure 1:
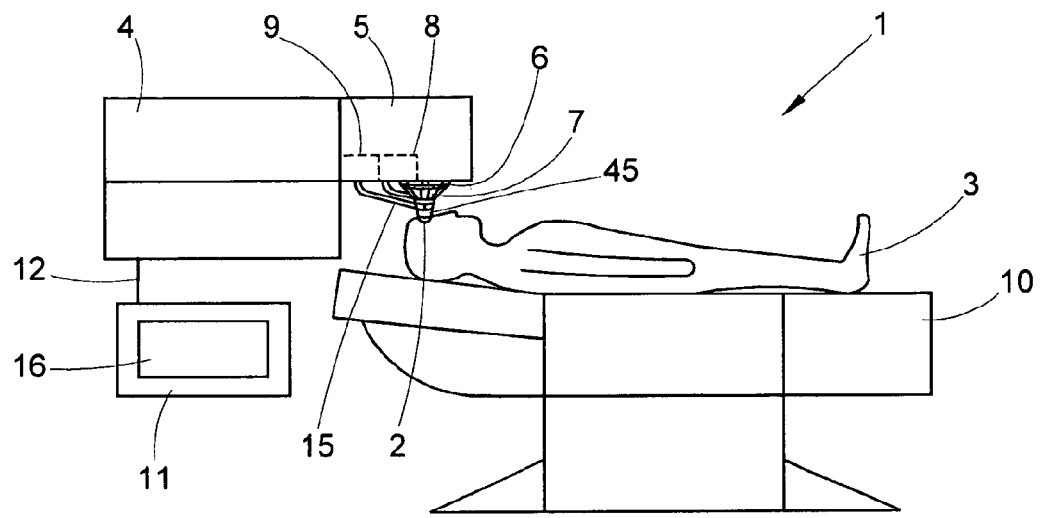
FIG. 1 depicts a schematic illustration of a treatment device that has a planning device for an eye surgery refraction correction treatment.

A treatment device for eye surgery is shown in FIG. 1 and labeled as a whole with the reference symbol 1. The treatment device 1 is configured to introduce laser incisions in an eye 2 of a patient 3. The treatment device 1 has a laser device 4 for this, which emits a laser beam 6 from a laser source 5, which is directed in the form of a focused beam 7 into the eye 2 or the cornea. The laser beam 6 is for example a pulsed laser beam with a wavelength of 300 nanometers to 10 micrometers. The pulse length of the laser beam 6 can also be between 1 femtosecond and 100 nanoseconds, wherein pulse repetition rates of 200 to 20,000 kilohertz—and pulse energies of 0.01 microjoules to 0.01 millijoules may be used. The treatment device 1 thus generates an incision in the cornea of the eye 2 by deflecting the pulsed laser beam. For this reason, there is also a scanner 8 and a beam intensity modulator 9 in the laser device 4, or its laser source 5.

The patient 3 is on a bed 10 that can be adjusted three dimensionally, in order to place the eye such that it is aligned with the laser beam 6. In a preferred structure, the position of the bed can be adjusted by operation of a motor. Alternatively, the treatment device can also be moved. The actuation can be obtained by application of a control unit 11 in particular, which fundamentally controls the operation of the treatment device 1 and is connected to the treatment device for this reason via suitable data connections, e.g., connecting lines 12. This communication can of course also take place by different approaches, e.g., waveguides, or through wireless technology. The control unit 11 adjusts the timing of the treatment device 1, in particular the laser device 4, thus producing corresponding functions in the treatment device 1.

The treatment device 1 also has a securing device 15, which fixes the position of the cornea of the eye 2 in relation to the laser device 4. This securing device 15 can comprise a known contact lens 45, which is placed on the cornea and fixed in place through application of suction, giving the cornea a desired geometric shape. Such contact lenses are known to the person skilled in the art from the prior art, e.g., DE 10 2005 040338 A1. The disclosure of this document is incorporated by reference herein in its entirety insofar as the description relates to a possible shape of the contact lens 45 for the treatment device 1.

The treatment device 1 also has a camera, not shown herein, which can record an image of the cornea 17 through the contact lens 45. The lighting for the camera can be in both the visible light spectrum as well as the infrared light spectrum.

The control unit 11 in the treatment device 1 also has a planning device 16, which shall be explained in greater detail below.

Figure 2:
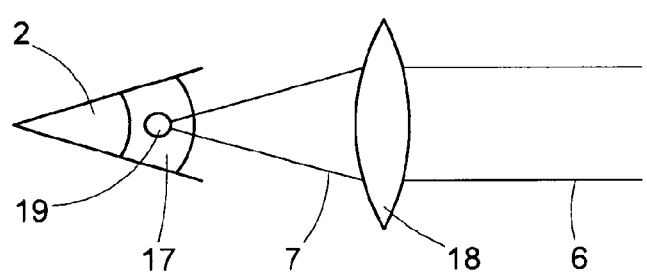
FIG. 2 depicts a schematic illustration of the effects of the laser beam used in the treatment device shown in FIG. 1.

FIG. 2 schematically shows the effects of the incident laser beam 6. The laser beam 6 is focused and enters the cornea 17 of the eye 2 as a focused laser beam 7. There is a lens 18, illustrated schematically, for focusing. It focuses the laser beam in the cornea 18, in which the laser beam energy density is so high that in combination with the pulse length of the pulsed laser beam 6, a non-linear effect is obtained in the cornea 17. By way of example, each pulse of the pulsed laser beam 6 can generate an optical breach in the cornea 17 in the focal point 19, which in turn triggers a plasma bubble, only schematically indicated in FIG. 2. When the plasma bubble is formed, the tissue separation comprises a larger area than the focal point 19, although the conditions for generating the optical breach are only obtained in the focal point 19. In order for an optical breach to be generated by each laser pulse, the energy density, i.e., the fluences of the laser beam lie above a certain pulse-dependent threshold. This relationship is known to the person skilled in the art, e.g., from DE 69500997 T2. Alternatively, a tissue separating effect can also be obtained through pulsed laser beams in that numerous laser beams are emitted in a region where the focal points overlap. In this case, numerous laser beam pulses interact in order to obtain a tissue separating effect. The type of tissue separation implemented by the treatment device is no longer relevant to the following description, the only thing that is essential is that an incision is generated in the cornea 17 of the eye 2.

In order to correct refraction through eye surgery, a cornea volume is removed by application of the laser beam 6 from a region inside the cornea 17 in that tissue layers are separated there that isolate the cornea volumes, thus enabling the removal thereof. In order to isolate the cornea volume that is to be removed, the position of the focal point 17 of the focused laser beam 7, e.g., is moved in the cornea when the laser beam is pulsed. This is shown schematically in FIG. 3. The refraction properties of the cornea 17 are modified in a targeted manner through the removal of the volume, in order to thus obtain the refraction correction. The volume is therefore usually in the shape of a lens and referred to as a lenticule.

Figure 3:
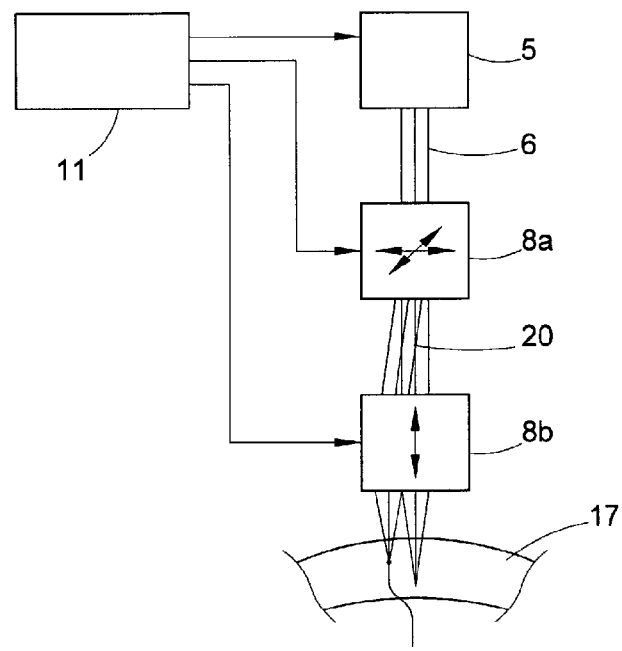
FIG. 3 depicts another schematic illustration of the treatment device shown in FIG. 1 with regard to the introduction of the laser beam.

The elements of the treatment device 1 are only labeled in FIG. 3 if they are necessary for understanding the incision generation. The laser beam 6 is focused into a focal point 19 in the cornea 19, as explained above, and the position of the focal point 19 is moved in the cornea such that focused energy from the laser beam pulses enters the tissue of the cornea 17 at various locations in order to generate an incision. The laser beam 6 for example exits the laser source 5 as a pulsed laser beam. The scanner 8 has a dual structure in FIG. 3, and comprises an xy-scanner 8a, which is obtained by two substantially orthogonal deflecting galvanometer mirrors in one variation. The scanner 8a deflects the laser beam 6 from the laser source 5 two dimensionally, such that there is a deflected laser beam 20 downstream of the scanner. The scanner 8a thus moves the position of the focal point 19 substantially perpendicular to the main direction of incidence of the laser beam 6 in the cornea 17. In order to move the depth there is also a z-scanner 8b, in addition to the xy-scanner 8a, in the scanner 8, in the form of an adjustable telescope, for example. The z-scanner 8b ensures that the z-position of the location of the focal point 19, i.e., is position on the optical axis of incidence, is modified. The z-scanner 8b can be upstream or downstream of the xy-scanner.

The individual coordinates do not need to be assigned to the spatial directions for the functional principle of the treatment device 1, nor does the scanner 8a need to deflect the beams at axes that are at right angles to one another. Instead, any scanner that can move the focal point 19 in a plane that does not contain the axis of incidence for the optical beam can be used. Furthermore, arbitrary, non-Cartesian coordinate systems can be used for deflecting or controlling the position of the focal point 19. Examples thereof are spherical coordinates or cylindrical coordinates. The position of the focal point 19 is controlled by the scanners 8a, 8b actuated by the control unit 11, which adjusts the laser source 5, the (not shown in FIG. 3) modulator 9, and the scanner 8. The control unit 11 ensures that the laser source is operated appropriately, and moves the focal point three dimensionally, indicated here by way of example, such that an incision is ultimately obtained that isolates a specific cornea volume that is to be removed for refraction correction.

Figure 4:
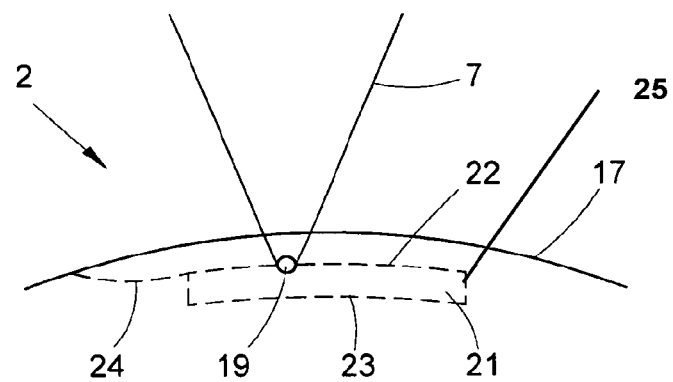
FIG. 4 depicts a schematic sectional view through the cornea illustrating the removal of the cornea volume in conjunction with the eye surgery refraction correction.

The control unit 11 works according to the control data, which are defined by the laser device 4, shown here merely by way of example, as the target point for the focus adjustment. The control data are normally combined to form a control data set. This results in geometric guidelines for the incision that is to be formed, e.g., the coordinates of the target point in the form of a pattern. The control data set then also contains concrete control values for the focus adjustment mechanism in this embodiment, e.g., for the scanner 8. The generation of the incision with the treatment device 1 is shown by way of example in FIG. 4. A cornea volume 21 in the cornea 17 is isolated by moving the focal point 19 in which the beam 7 is focused. For this, incisions are formed, e.g., as anterior flap incisions 22 and posterior lenticule incisions 23. These terms are only to be understood herein by way of example, in order to establish the reference to the conventional LASIK or FLEX methods, for which the treatment device 1 is likewise configured, as explained above. The only essential thing here is that the incisions 22 and 23 and the encompassing edge incision 25, which joins the incisions 22 and 23 at their edges, isolate the cornea volume 21. A cornea flap bordering on the cornea volume at the back can also be folded away through an incision 24, such that the cornea volume 21 can be removed. Alternatively, and substantially to the present invention, the SMILE method can be used, in which the cornea volume 21 is removed through a small incision, as is described in DE 10 2007 019813 A1. The disclosure of this document is incorporated herein by reference in its entirety.

Figure 5:
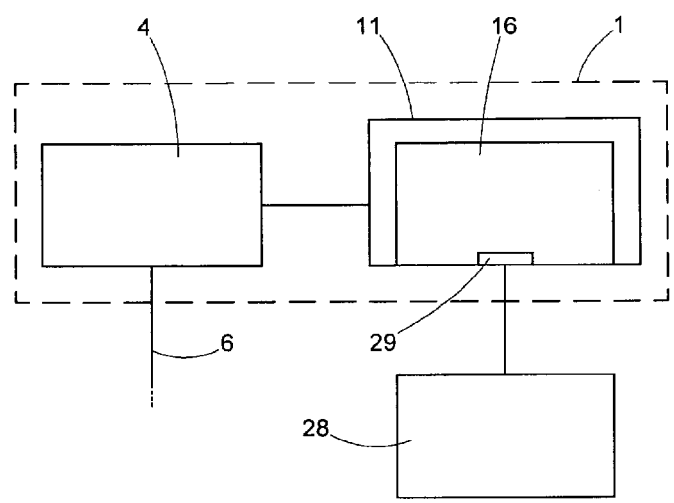
FIG. 5 depicts a schematic illustration regarding the structure of the treatment device shown in FIG. 1, with particular reference to the planning device located therein.

FIG. 5 schematically shows the treatment device 1, in reference to which the significance of the planning device 16 shall be explained in greater detail. The treatment device 1 has at least two elements or modules in this variation. The laser device 4 explained above emits the laser beam 6 onto the eye 2. The laser device 4 is operated fully automatically by the control unit 11, as explained above, i.e., the laser device 4 initiates the generation deflection of the laser beam 6 in response to a starting signal, and generates incisions formed in the manner described above. The control signals necessary for the operation of the laser device are received by the laser device 4 from the control unit 11, which already has the corresponding control data. This takes place by application of the planning device 16, which is shown merely by way of example in FIG. 5 as a component of the control unit 11. The planning device 16 can of course also be in the form of an independent element and communicate with the control unit 11 in a hard-wired or wireless manner. The only essential thing here is that there is an appropriate data transmission channel between the planning device 16 and the control unit 11.

The planning device 16 generates a control data set provided to the control unit 11 for executing the eye surgery refraction correction. The planning device uses measurement data regarding the cornea of the eye for this. This data comes from a measurement device 28 in the embodiment described herein, which has already measured the eye 2 of the patient 3. The measurement device 28 can of course have an arbitrary design and transmit the corresponding data to the interface 29 in the planning device 16. In particular, the measurement device 28 is in the form of an OCT or ultrasound measurement system, or a confocal laser scanning system, in order to provide the measurement data with the necessary precision.

The planning device helps the operator of the treatment device 1 in determining the incision for isolating the cornea volume 21. This can result in a fully automatic determination of the incision, which can be obtained in that the planning device 16 determines the cornea volume 21 that is to be removed from the measurement data, the boundary surfaces of which are defined as the incision area and generates corresponding control data for the control unit 11 therefrom. At the other end of the degree of automation, the planning device 16 can provide input options at which a user inputs the incisions in the form of geometric parameters, etc. Intermediate steps provide proposals for the incisions, which are generated automatically by the planning device 16 and can then be modified by a technician. Fundamentally, all of the concepts that have been explained above in the general description can be implemented here in the planning device 16.

In order to treat a patient, the planning device 16 generates control data for generating the incision, which are then used in the treatment device 1.

Figure 6A:
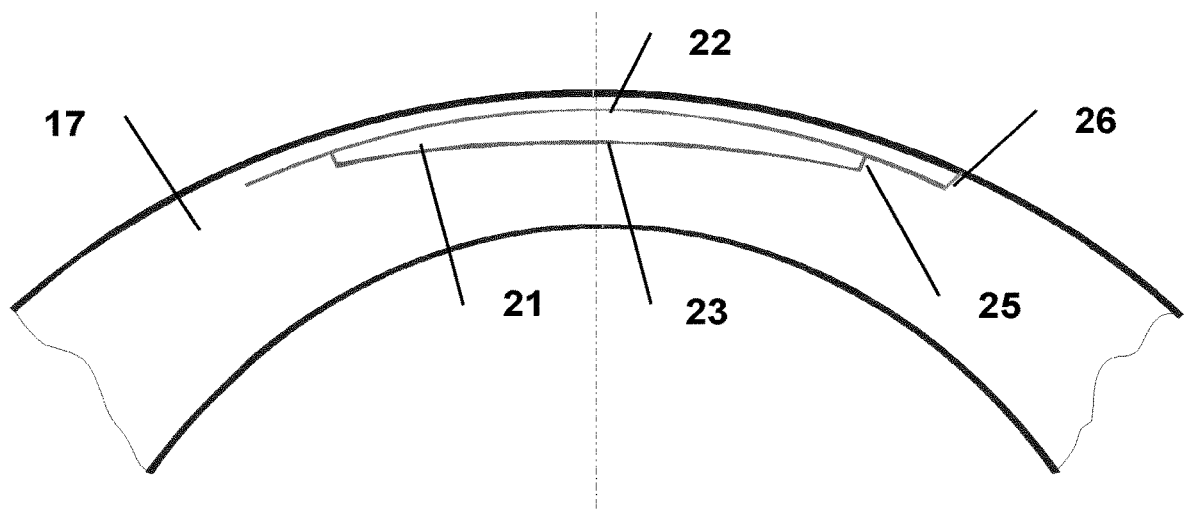
FIGS. 6A and 6B depict in cross section and in frontal view respectively schematic illustrations of a lenticule geometry SMILE with an incision that is to be introduced according to the prior art.
Figure 6B:
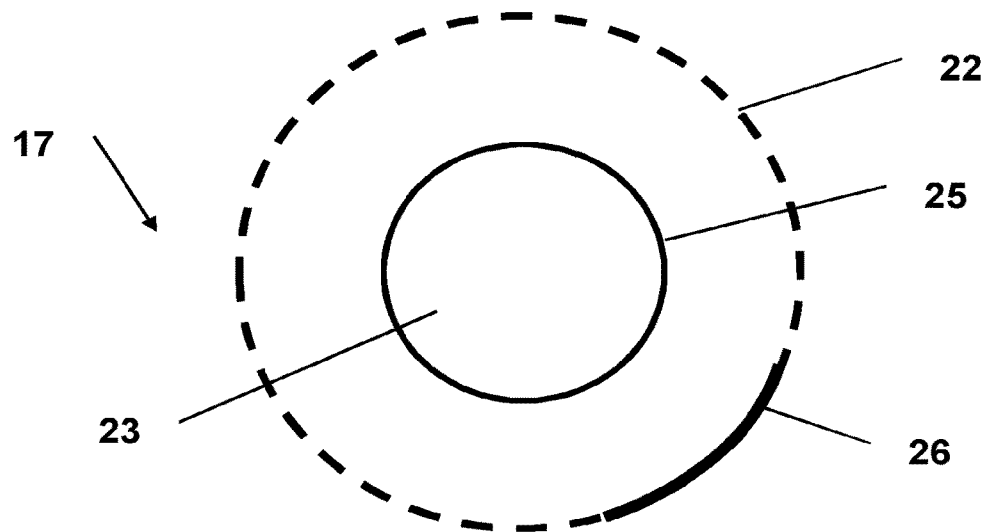

FIG. 6A is a schematic illustration of a cornea cross section in a SMILE procedure, in order to illustrate the geometric relationships. The cornea 17 has an anterior cap incision 22 with an opening incision 26. The posterior lenticule incision 23 isolates the lenticule volume 21, which can then be removed through the opening incision 26. If it is then necessary to carry out a second refractive treatment, a new lenticule must be calculated. For this, the position and shape of the cap incision 22 in the original treatment must be determined with the necessary precision. This can be achieved in a first variation of the invention through a measurement with the measurement device 28. The type of such measurement is known in principle from DE 103 23 422 A1, which is incorporated by reference in its entirety herein. In this document, the measurement device is used for something else, however, specifically the self-calibration of the treatment laser during the treatment in order to ensure the necessary precision (better than 5 µm). The principle of the ultrasound measurement is explained in "Refractive Surface Ablation: PRK, LASEK, Epi-lasik, Custom, PTK, and Retreatment" by Paolo Vinciguerra, Fabrizio Camesasca— Chapter 36 Dan Z. Reinstein, Ronald H. Silverman, Timothy J. Archer—"Very high frequency digital ultrasound: artemis 2 scanning in corneal refractive surgery," SLACK Inc. Thorofare, NJ, USA, 2007, the obtained measurement precision is 1 µm, and is therefore suitable for the present task. A new lenticule incision 23 and a new boundary incision 25 are calculated in the planning device 16 from the current position of the cap incision 22 and the present requirements of the refractive correction, and the incisions are made in the cornea 17 by application of the treatment device 1.

The position and shape of the reference area in relation to the front surface of the cornea, i.e., the depth of the original cap incision 22, can change after the operation through epithelial hyperplasia (Heck's disease), changes in the tear film, swelling of the cornea, edema in the cornea, etc. In particular, a change in the thickness of the epithelial layer ΔThickness (x, y) or ΔThickness (r, φ)) causes a corresponding change in the relative position of the original cap incision in relation to the surface of the cornea.

Changes such as swellings, changes in the tear film, etc. can also take place when the operation is aborted (e.g., due to a loss of vacuum in the contact lens) and must likewise be taken into account.

In a first variation of the invention, the changes (changes in the epithelium thickness as a result of the primary treatment, relative changes in the position of the incision formed in the primary treatment, e.g., due to epithelial hyperplasia) are measured with the measurement device 28 and incorporated in the calculation of the new lenticule incision 23.

Figure 7:
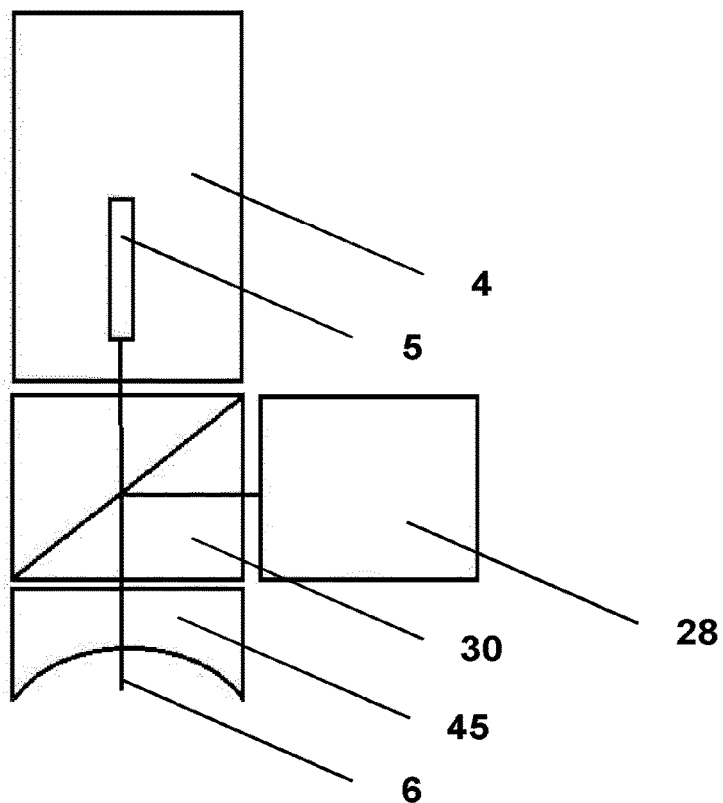
FIG. 7 depicts a schematic illustration regarding the structure of the treatment device shown in FIG. 5, with particular reference to the measurement device located therein.

FIG. 7 shows a schematic illustration of the structure of the treatment device in FIG. 5 and the coupling thereof to the measurement device 28. The laser device 4 has a laser source 5, which generates a laser beam 6. A contact lens 45 is used for docking to the eye, not shown herein. The measurement device 28 is coupled thereto with a coupling element 30. The coupling element 30 can be in the form of an optical waveguide for an optical measurement device 28 (OCT, confocal laser scanning system). With an ultrasound measurement device 28, the coupling element forms an acoustic waveguide, as described, e.g., in EP 343 432 A2.

The measurement of the reference area of the previous incision (primary interface) enables a precise alignment of the old and new incisions, even if the new treatment is decentered and skewed in relation to the original treatment.

For this, an imaging or measurement of the docked cornea is generated during the original treatment and stored temporarily in a data base. If a post-treatment (re-treatment) takes place, a new image or measurement of the docked eye is generated and compared with the stored image or measurement.

In a simple expansion stage, a simple comparison of the old incision with the planned new incision can first take place, and the system checks whether a re-treatment is possible therewith. An output to the user informs him whether he can carry out the post-treatment or not.

In one embodiment, the old incision is taken into account in calculating the new firing pattern, and effects such as described above are accounted for. As a result, a specially adapted treatment (customized treatment) can be carried out in accordance with the conditions present in the cornea of the patient.

The re-treatment for example takes place with a single incision, because it is not necessary to maintain a distance to the previous incision, thus preserving cornea tissue, such that the boundary to the remaining stroma thickness of 250 μm is not reached too quickly. A renewed treatment beneath the first incision can also be improved by application of imaging the previous incision, because the access incision to the new lenticule can start at the old access incision, and it is not necessary to make a new incision in the surface. This does not weaken the cornea further, in the manner that a new incision would.

The change in thickness in the epithelial layer is taken into account in planning the lenticule incision 23 according to the invention. In the first variation of the invention, this takes place through taking the results of a measurement of the position of the original cap incision into account. In a second variation of the invention, the complexity is reduced in that the typical changes due to the pretreatment are predicted on the basis of treatment parameters and taken into account for the re-treatment. The change in thickness is known per se for a myopia correction by means of the SMILE method, e.g., from N. Luft, M. H. Ring, M. Dirisamer, A. S. Mursch-Edlmayr, T. C. Kreutzer, J. Pretzl, M. Bolz and S. G. Priglinger, "Corneal epithelial remodeling induced by Small Incision Lenticular Extraction (SMILE)," Invest Ophthalmol Vis Sci., issue 47, no. 9, pp. 176-183, 2016. It is shown therein that the epithelial layer becomes thicker after an operation. It is obvious that the extent of this change correlates to the type of change and the extent of correction, and the dynamics correspond to the course of the healing process, starting with the treatment and lasting at least until reaching a refraction that is stable in the long-term. According to Luft et al. the extent of the observed thickening reaches a value of a few micrometers after approx. 3 months. It can be assumed therefrom that this value changes very little after this. The data allow it to be concluded that the epithelial thickening in SMILE procedures for myopia correction take place in a nearly identical manner and may depend on the age of the patient.

$$\Delta Thickness = \Delta Thicknesss\ (\Delta SE, age).$$

$$\Delta Thickness = 0.707\ \mu m + 1.268\ \mu m/dpt \Delta SE - 0.038\ \mu m/(dpt^*y)\Delta SE^*(Age-30y).$$

If the thickening on the surface of the cornea $\Delta Thickness\ (r, \phi)$ is not uniform, as was observed in a work appearing at around the same time by S. Ganesh, "Epithelial thickness Profile Change Following Small Incision Refractive Lenticule Extraction (SMILE) for Myopia and Myopic Astigmatism," JRS, issue 32, no. 7, pp. 473-478, 2016, this can result in a greater refractive change in the course of healing after a treatment than if it is uniform, as was observed by Luft et al. A refractive change can also affect both spheres and cylinders, as well as aberrations of a higher order. A non-homogenous change in thickness is more difficult to take into account in the planning of a post-treatment.

The incisions of the post-treatment must be positioned correctly in relation to the incisions of the primary treatment. This pertains to all three spatial dimensions. For this reason, the device calculates a standard post-treatment, based on the data from the primary treatment, and proposes it to the user. By using treatment data from the primary treatment, the planning of the post-treatment is made in relation to the coordinate system in the primary treatment. The coordinate system of the second treatment is normally at least displaced and/or skewed in relation to the primary treatment, however. Such a displacement is to be taken into account according to the invention. In the following, coordinate systems always refer to eye coordinate systems.

These displacements can therefore have different causes:
1. A deviation between the device coordinate system and the eye coordinate system in the primary treatment;
2. A deviation between the device coordinate system and the eye coordinate system in the secondary treatment;
3. A deviation between the device coordinate systems in the primary and secondary treatments;
4. A deviation between the eye coordinate systems in the primary and secondary treatments.

Figure 8:
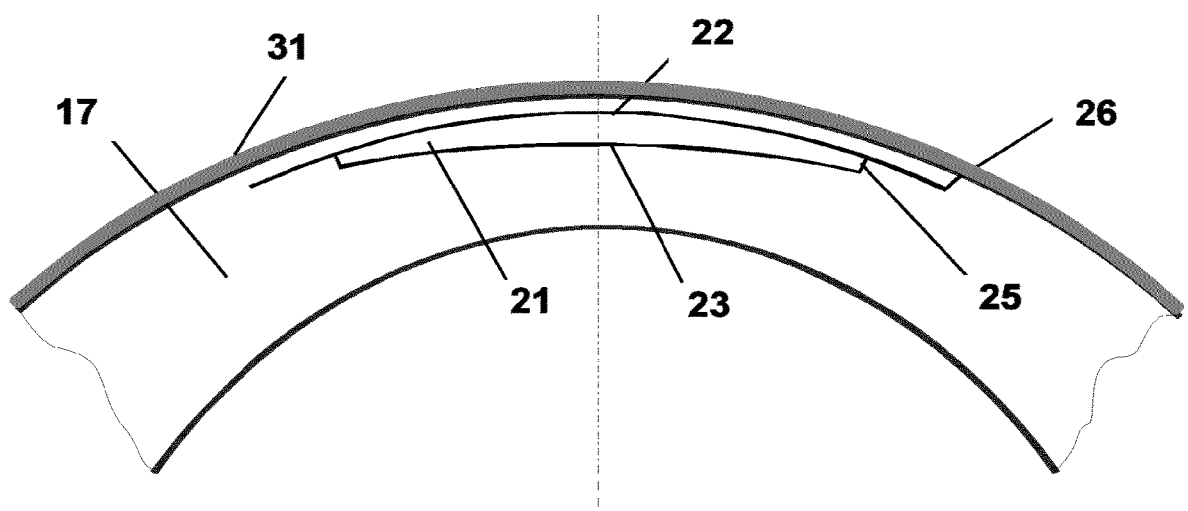
FIG. 8 depicts a schematic illustration of a lenticule geometry for correction according to the invention.
Figure 9:
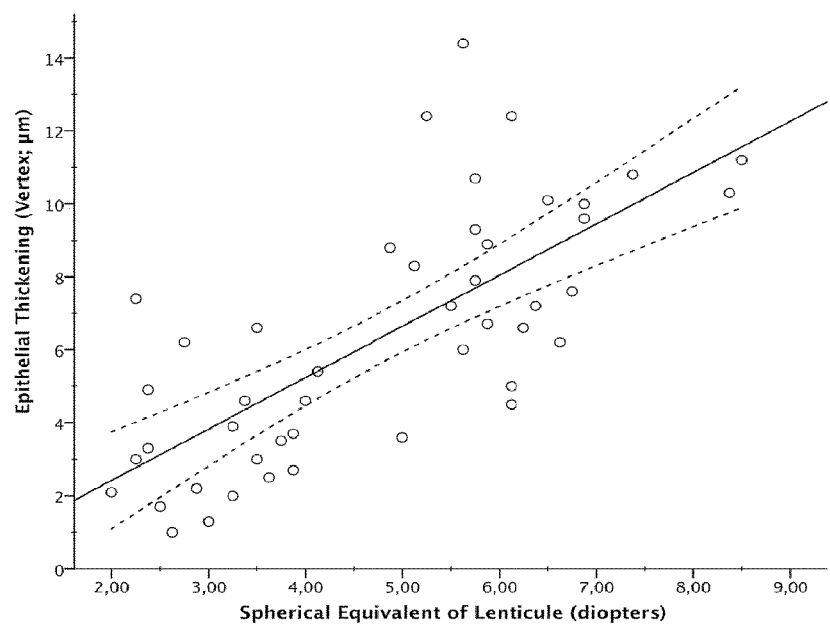
FIG. 9 depicts a schematic illustration of the relationship between epithelial thickening and refraction correction.

A first variation of the incision provides that a secondary lenticule incision 23 is made below (posterior to) the existing interface (cap incision 22 in the primary treatment), and connected to the existing interface through the lenticule edge incision 25. As a result, a lenticule is created that can be subsequently extracted manually. This variation is shown in FIG. 8, wherein the thickening of the epithelium 31 is roughly indicated.

A second variation of the incision provides that a secondary lenticule incision is made above (anterior to) the existing interface, and connected to the existing interface through a lenticule edge incision. The lenticule edge incision is advantageously made laterally in front of the lenticule incision. As a result, the lenticule can in turn be extracted manually.

It is important for both variations of the incision that the new incision is as close as possible to the existing incision. Because of the displacements of the coordinate systems the lateral and axial positions of the existing interface can only be predicted in the secondary treatment with limited precision. This can result in two substantial problems:
1. The lenticule generated through the interactions of the old and new incisions is not the right shape for the intended refractive correction. In this case, the correction deviation may reduce the efficacy of the procedure.
2. The old and new incisions do not result in a complete separation of the lenticule, because they do not touch or cut it. In this case the lenticule extraction may fail entirely.

In one example embodiment of the invention, the edge incision in the secondary treatment is extended for this reason, such that it definitely crosses the existing interface. By way of example, the edge incision in the first variation of the incision is extended in the interior of the primary (and secondary) cap, such that a cross cut is obtained with the existing interface, i.e. the edge incision 25 intersects the cap incision 22 (not shown in this manner in FIG. 8). As a result, axial position errors can be compensated for. This is particularly important because the change in the epithelium caused by the primary treatment mainly cause an axial displacement between the eye coordinate systems of the primary and secondary treatments.

In another embodiment of the invention the displacement caused by the change in the epithelium is estimated and compensated for. This estimation is based on from the primary treatment, in particular the intended and/or targeted refraction modification, the age of the patient, and a keratometry. An approximation formula known from Luft et al. for example, or some other approximation formula that can also take into account non-homogenous thickening, can be used for estimating the displacement caused by the change in the epithelium. The displacement of the interface in relation to the planned position in the primary treatment can be calculated accordingly. By way of example, a homogenous thickening of the epithelium ultimately results in a homogenous displacement of the existing interface in relation to the device coordinate system for the post-treatment. This situation is accounted for in the post-treatment in that the lenticule incision is displaced, tilted, or curved accordingly.

In another embodiment of the invention, the change in the epithelium (epithelial hyperplasia) can take place, for example, with high resolution OCT or ultrasound measurement device. The post-treatment is then adjusted in that the lenticule incision 23 is curved and positioned accordingly. In particular the secondary lenticule surface can be formed with the desired refractive effect, as with a primary treatment, in that the virtual cap surface of the secondary treatment, which serves as the primary interface and therefore will not be cut again, is spatially placed over the existing interface of the primary treatment in order to calculate the correct lenticule incision in terms of shape and position. Alternatively, a quantified deviation can be compensated for by a corresponding allowance in the secondary treatment.

In another embodiment of the invention, the displacement caused by the change in the epithelium (epithelial hyperplasia) is measured and the position of the new incision is corrected accordingly. The position and shape of the existing interface can be measured with a high resolution OCT or ultrasound measurement device, as shown in FIG. 7. The post-treatment is then adjusted in that the lenticule incision 23 is curved and positioned accordingly. In particular, the lenticule surface can be formed with the desired refractive effects, as in the primary treatment, in that the virtual cap surface of the secondary treatment, which already serves as the interface and therefore will not be cut again, is spatially placed over the existing interface from the primary treatment in order to calculate the correct lenticule incision in terms of shape and position.

The embodiments described above can be implemented individually or combined with one another. The combination offers the additional possibility for calculating deviations among the different planning methods. This information can be used not only for testing for plausibility. Instead, crosscuts can also be derived, the size of which is adjusted to the imprecision of the various calculating methods.

In a further development of the invention, the position and shape of the interface obtained in the primary treatment is calculated in reference to the coordinate system of the treatment device. If, for example, a contact lens is used that is fixed in place with a vacuum, it is sufficient to determine the depth of the interface as a function of the location in relation to the surface of the eye. This is not difficult with a high resolution OCT. The data $T(r, \phi)$ that are then obtained are normally rotationally symmetrical, and can be approximated satisfactorily with a rotationally symmetrical polynomial P(r). The lenticule incision $L(r, \phi)$ is first calculated, e.g., for the first variation of the incision assuming a homogenous cap with a thickness D, to which the function $P(r)-D$ is subsequently applied. The resulting lenticule incision $L'(r, \phi)=L(r, \phi)+P(r)-D$ is corrected with respect to the displacement of the primary interface in relation to the surface of the eye caused by the epithelial remodeling. This correction method according to the principle of an interference calculation can be refined incrementally by the person skilled in the art.

In another embodiment, the new incisions can be displayed to the user in a simulated cross section image of the cornea, in conjunction with the incisions from the primary treatment. Moreover, the existing information regarding anatomical changes is used for calculating a correction of the display. The epithelial thickening can be derived, for example, from difference between the pre-operative pachymetry, the lenticule thickness (or the lenticule profile) in the primary treatment, and the current pachymetry. This simple estimation can be supplemented with further information, e.g., a measured epithelium thickness, an epithelium thickness profile, a sub-epithelial topography, or a high resolution cross sectional image (OCT image (B-scan), Scheimpflug, etc.), and the course of the interface identified therein with respect to the front surface of the cornea. The geometric imprecision of the incision is depicted in a suitable manner (e.g., error bars or semitransparent broadenings of an affected element in the depiction). False or critical geometries are visually highlighted (e.g., warning signs).

Because the refractive effect of the secondary lenticule is directly related to its shape, a positioning error in the secondary treatment in relation to the existing incisions affects the refractive effect of the secondary lenticule. For this reason, the expected refraction of the lenticule, including the positioning error and variance of the refractive effect resulting from the change in epithelium thickness, can be displaced in a further development of the invention. The user has the possibility of optimizing this accordingly, in order to plan a target refraction while still taking possible errors into account. By way of example, a displacement of the target refraction into the region of very small hyperopia can take place, taking into account the existing accommodating capacity of the eye (in young patients).

The planning device visualizes the incision geometry in a virtual display of the existing geometric situation on the eye, and the superimposed depiction of the planned incision. The incisions from the primary treatment are also shown. In a further development, the imprecision of the position of this incision is visualized in a suitable manner (e.g., error bars, semitransparency, imaging).

The planning device can contain a prognosis model for typical post-operative anatomical changes according to SMILE, which serves in the treatment planning of a SMILE post-correction as the starting point ("estimation $1^{st}$ order"). Diagnosis data (topography, wave front, pachymetry, OCT, Scheimpflug) obtained immediately prior to the secondary treatment can be used for refining the planning ("estimation $2^{nd}$ order"). Intra-operative diagnosis data (OCT after docking) can likewise be drawn on. The different input information may also be used only for confirming the plan already made, or for estimating errors and a prognosis.

The prognosis of the refractive effect can extend beyond the (mean) target refraction, and can also comprise displacements and expected diffusion. The various causes of deviations can be drawn on for this.

It should also be noted that the treatment device 1 and the planning device 16 are concretely implemented for executing the method explained in general above.

A further embodiment of the planning device is in the form of a computer program, or a corresponding data medium with a computer program that implements the planning device on a corresponding computer such that the input of the measurement data to the computer takes place via a suitable data transmitting channels, and the control data are transmitted from this computer to the control unit 11, for which the person skilled in the art can make use of known data transmitting implements.

The invention claimed is:

1. A system comprising:
a laser treatment device for eye surgery; and
a planning device that generates control data for eye surgery, the planning device comprising:
a calculating processor that determines the at least one incision in the cornea selected from a group of planned cuts consisting of a cap incision, a lenticule incision, an access incision and a combination of the foregoing, the cap incision and the lenticule incision together at least partially circumscribing and at least partially isolating a lenticule that can be removed from the cornea via the access incision;
wherein the calculating processor is operably coupled to a viewable visual display and wherein the calculating processor controls the visual display to display an image of at least one of the planned cuts to be applied in treatment overlying an image of the cornea to be treated, the image of the cornea to be treated also depicting an image of incisions from an earlier primary treatment wherein at least one of the image of the planned cuts and the image of the incisions from the earlier primary treatment includes a visual depiction of geometric imprecision of at least one of the planned cuts and the image of the incisions from the earlier primary treatment;
wherein the calculating processor uses information related to the planned cuts and the geometric imprecision to plan intersecting cross cuts of an edge incision and to generate a control data set to execute the intersecting cross cuts that are planned;
wherein the planning device is configured to transmit the control data set to the laser treatment device to make the at least one incision, the intersecting cross cuts, or both in the cornea.

2. The planning device as claimed in claim 1, wherein the visual depiction of geometric imprecision of the at least one of the image of the planned cuts and the image of the incisions from the earlier primary treatment comprises error bars, semitransparent broadening or imaging.

3. The planning device as claimed in claim 1, wherein the calculating processor takes into account an estimated displacement caused by a prior change in a corneal epithelium of the eye and compensates for the estimated displacement caused by the prior change in a corneal epithelium.

4. The planning device as claimed in claim 3, wherein the calculating processor displaces the expected refraction of the lenticule including positioning error and variance of refractive effect caused by the prior change in the corneal epithelium.

5. The planning device as claimed in claim 3, wherein the calculating processor supplements the estimated displacement with further information selected from a group consisting of measured epithelial thickness, an epithelial thickness profile, a subepithelial topography of a cap incision, and a high resolution cross sectional image, a course of an interface identified in the cornea with respect to the front surface of the cornea and a combination of the foregoing.

6. The planning device as claimed in claim 3, wherein the calculating processor supplements the estimated displacement with further information from a high resolution cross sectional image received from an imaging device selected from a group consisting of an OCT, an OCT B-scan, a Scheimpflug camera, an ultrasound measurement system, a confocal laser scanning system and a combination of the foregoing.

7. A treatment device for eye surgery, comprising:
a laser device, which generates the at least one incision in the cornea by application of a laser beam in accordance with control data, and
a planning device that generates control data for a treatment device for eye surgery, the treatment device generating at least one incision in a cornea to be treated by application of a laser device, the planning device comprising:
a calculating processor that determines the at least one incision in the cornea selected from a group of planned cuts consisting of a cap incision, a lenticule incision, an access incision and a combination of the foregoing, the cap incision and the lenticule incision together at least partially circumscribing and at least partially isolating a lenticule that can be removed from the cornea via the access incision;
wherein the calculating processor is operably coupled to a viewable visual display and wherein the calculating processor controls the visual display to display an image of at least one of the planned cuts to be applied in treatment overlying an image of the cornea to be treated, the image of the cornea to be treated also depicting an image of incisions from an earlier primary treatment wherein at least one of the image of the planned cuts and the image of the incisions from the earlier primary treatment includes a visual depiction of geometric imprecision of at least one of the planned cuts and the image of the incisions from the earlier primary treatment;
wherein the calculating processor uses information related to the planned cuts and the geometric imprecision to plan intersecting cross cuts of an edge incision and to generate a control data set to execute the intersecting cross cuts that are planned; and
wherein the planning device is configured to transmit the control data set to the laser device and the control data set is used to operate the laser device thereby generating the at least one incision, the intersecting cross cuts or both in the cornea by operation of the laser device.

8. The treatment device as claimed in claim 7, wherein the visual depiction of geometric imprecision of the at least one of the image of the planned cuts and the image of the incisions from the earlier primary treatment comprises error bars, semitransparent broadening or imaging.

9. The treatment device as claimed in claim 7, wherein the calculating processor takes into account an estimated displacement caused by a prior change in a corneal epithelium of the eye and compensates for the estimated displacement caused by the prior change in a corneal epithelium.

10. The treatment device as claimed in claim 9 wherein the calculating processor displaces the expected refraction of the lenticule including positioning error and variance of refractive effect caused by the prior change in the corneal epithelium.

11. The treatment device as claimed in claim 9, wherein the calculating processor supplements the estimated displacement with further information selected from a group consisting of measured epithelial thickness, an epithelial thickness profile, a subepithelial topography of a cap incision, and a high resolution cross sectional image, a course of an interface identified in the cornea with respect to the front surface of the cornea and a combination of the foregoing.

12. The treatment device as claimed in claim 9, wherein the calculating processor supplements the estimated displacement with further information from a high resolution cross sectional image received from an imaging device selected from a group consisting of an OCT, an OCT B-scan, a Scheimpflug camera, an ultrasound measurement system, a confocal laser scanning system and a combination of the foregoing.

13. A method that generates control data for a treatment device for eye surgery, the treatment device generating at least one incision in a cornea to be treated by application of a laser device, the method comprising:
   determining at least one incision in the cornea selected from a group of planned cuts consisting of a cap incision, a lenticule incision, an access incision and a combination of the foregoing, the cap incision and the lenticule incision together at least partially circumscribing and at least partially isolating a lenticule that can be removed from the cornea via the access incision;
   controlling a viewable visual display to display an image of at least on of the planned cuts to be applied in treatment overlying an image of the cornea to be treated, the image of the cornea to be treated also depicting an image of incisions from an earlier primary treatment;
   controlling the viewable visual display to depict at least one of the image of the planned cuts and the image of the incisions from the earlier primary treatment to include a visual depiction of geometric imprecision of at least one of the planned cuts and the image of the incisions from the earlier primary treatment;
   using information related to the planned cuts and the geometric imprecision to plan intersecting cross cuts of an edge incision and to generate a control data set to execute the intersecting cross cuts that are planned; and
   transmitting the control data set to the laser device and using the control data set to operate the laser device thereby generating the at least one incision, the intersecting cross cuts or both in the cornea by operation of the laser device.

14. The method as claimed in claim 13, further comprising controlling the visual depiction of geometric imprecision of the at least one of the image of the planned cuts and the image of the incisions from the earlier primary treatment by depicting error bars, semitransparent broadening or imaging.

15. The method as claimed in claim 13, further comprising taking into account an estimated displacement caused by a prior change in a corneal epithelium of the eye and compensating for the estimated displacement caused by the prior change in a corneal epithelium.

16. The method as claimed in claim 15, further comprising displacing the expected refraction of the lenticule including positioning error and variance of refractive effect caused by the prior change in the corneal epithelium.

17. The method as claimed in claim 15, further comprising supplementing the estimated displacement with further information selected from a group consisting of measured epithelial thickness, an epithelial thickness profile, a subepithelial topography of a cap incision, and a high resolution cross sectional image, a course of an interface identified in the cornea with respect to the front surface of the cornea and a combination of the foregoing.

18. The method as claimed in claim 15, further comprising supplementing the estimated displacement with further information from a high resolution cross sectional image received from an imaging device selected from a group consisting of an OCT, an OCT B-scan a Scheimpflug camera, an ultrasound measurement system, a confocal laser scanning system and a combination of the foregoing.

* * * * *